(12) United States Patent
Mori et al.

(10) Patent No.: US 7,758,532 B2
(45) Date of Patent: Jul. 20, 2010

(54) BLOOD PURIFICATION DEVICE

(75) Inventors: Yoshihiro Mori, Shizuoka (JP); Takayuki Ohishi, Shizuoka (JP)

(73) Assignee: Nikkiso Co., Ltd. (JP)

( * ) Notice: Subject to any disclaimer, the term of this patent is extended or adjusted under 35 U.S.C. 154(b) by 490 days.

(21) Appl. No.: 10/713,772

(22) Filed: Nov. 14, 2003

(65) Prior Publication Data

US 2004/0129616 A1 Jul. 8, 2004

(30) Foreign Application Priority Data

Nov. 14, 2002 (JP) ............................ 2002-330984
Oct. 17, 2003 (JP) ............................ 2003-358200

(51) Int. Cl.
*A61M 37/00* (2006.01)

(52) U.S. Cl. ..................................... 604/5.01; 604/6.06

(58) Field of Classification Search ................ 604/5.01, 604/6.06, 4.01
See application file for complete search history.

(56) References Cited

U.S. PATENT DOCUMENTS

| | | | | |
|---|---|---|---|---|
| 4,153,554 A | * | 5/1979 | von der Heide et al. | 210/96.2 |
| 4,469,593 A | * | 9/1984 | Ishihara et al. | 210/96.2 |
| 4,508,622 A | * | 4/1985 | Polaschegg et al. | 210/96.2 |
| 4,897,184 A | * | 1/1990 | Shouldice et al. | 210/87 |
| 4,923,598 A | * | 5/1990 | Schal | 210/87 |
| 4,966,691 A | * | 10/1990 | Brous | 210/87 |
| 4,967,754 A | * | 11/1990 | Rossi | 600/483 |
| 5,024,756 A | * | 6/1991 | Sternby | 210/93 |
| 5,081,658 A | * | 1/1992 | Imai et al. | 378/45 |
| 5,091,094 A | * | 2/1992 | Veech | 210/647 |
| 5,230,341 A | * | 7/1993 | Polaschegg | 600/481 |
| 5,331,958 A | * | 7/1994 | Oppenheimer | 600/322 |
| 5,366,630 A | * | 11/1994 | Chevallet | 210/645 |
| 5,399,157 A | * | 3/1995 | Goux et al. | 604/4.01 |
| 5,593,854 A | * | 1/1997 | Berndt | 435/31 |
| 5,690,831 A | * | 11/1997 | Kenley et al. | 210/646 |
| 5,730,720 A | * | 3/1998 | Sites et al. | 604/27 |
| 5,830,133 A | * | 11/1998 | Osten et al. | 600/322 |

(Continued)

FOREIGN PATENT DOCUMENTS

JP  09-149935 A1  6/1997

OTHER PUBLICATIONS

Patent Abstracts of Japan for JP09-149935 published on Jun. 10, 1997.

*Primary Examiner*—Tatyana Zalukaeva
*Assistant Examiner*—Paula L Craig
(74) *Attorney, Agent, or Firm*—McDermott Will & Emery LLP

(57) ABSTRACT

A blood purification device that does not require measurement of a patient's blood concentration performed ahead of time and that allows treatment time to be reduced, thus reducing the burden on the patient, and allows monitoring of problems in the internal elements. The present invention includes: blood purification device main units including a blood pump disposed in an arterial blood circuit, a blood purification device purifying blood, and an ultrafiltration pump for draining water from blood; first measuring means and second measuring means measuring hematocrit values and disposed at the arterial blood circuit and the venous blood circuit respectively; calculating means calculating a ratio for measured hematocrit values and a ratio for a theoretical hematocrit values determined from a predetermined equation and evaluating means evaluating whether the values determined by calculating means are roughly similar.

3 Claims, 6 Drawing Sheets

U.S. PATENT DOCUMENTS

| | | | |
|---|---|---|---|
| 6,059,979 A * | 5/2000 | Brown | 210/739 |
| 6,117,099 A * | 9/2000 | Steuer et al. | 604/4.01 |
| 6,126,831 A * | 10/2000 | Goldau et al. | 210/646 |
| 6,193,681 B1 | 2/2001 | Davidner et al. | 604/6.08 |
| 6,200,485 B1 * | 3/2001 | Kitaevich et al. | 210/739 |
| 6,217,539 B1 * | 4/2001 | Goldau | 604/4.01 |
| 6,508,111 B2 * | 1/2003 | Osaki et al. | 73/118.1 |
| 6,537,240 B2 * | 3/2003 | Cavicchioli et al. | 604/5.01 |
| 6,554,789 B1 * | 4/2003 | Brugger et al. | 604/6.11 |
| 6,579,253 B1 * | 6/2003 | Burbank et al. | 604/5.01 |
| 6,582,656 B1 * | 6/2003 | Steuer et al. | 422/44 |
| 6,794,194 B2 * | 9/2004 | Fava et al. | 436/66 |
| 6,821,441 B2 * | 11/2004 | Pedrini et al. | 210/739 |
| 6,890,315 B1 * | 5/2005 | Levin et al. | 604/6.09 |
| 7,131,956 B1 * | 11/2006 | Pirazzoli et al. | 604/6.09 |
| 7,170,591 B2 * | 1/2007 | Ohishi et al. | 356/39 |
| 7,381,195 B2 * | 6/2008 | Mori et al. | 604/6.08 |
| 7,537,688 B2 * | 5/2009 | Tarumi et al. | 210/96.2 |
| 2001/0037079 A1 * | 11/2001 | Burbank et al. | 604/6.09 |
| 2002/0121471 A1 * | 9/2002 | Pedrazzi | 210/321.71 |
| 2002/0123864 A1 * | 9/2002 | Eryurek et al. | 702/188 |
| 2002/0128545 A1 * | 9/2002 | Steuer et al. | 600/345 |
| 2002/0169514 A1 * | 11/2002 | Eryurek et al. | 700/110 |
| 2003/0016585 A1 * | 1/2003 | Leveque et al. | 366/88 |
| 2004/0054315 A1 * | 3/2004 | Levin et al. | 604/5.01 |
| 2004/0057037 A1 * | 3/2004 | Ohishi et al. | 356/39 |
| 2004/0067594 A1 * | 4/2004 | Mori et al. | 436/70 |
| 2004/0068219 A1 * | 4/2004 | Summerton et al. | 604/5.01 |
| 2006/0043007 A1 * | 3/2006 | Tarumi et al. | 210/96.2 |
| 2006/0138049 A1 * | 6/2006 | Kim et al. | 210/646 |
| 2007/0083145 A1 * | 4/2007 | Murakami et al. | 604/6.09 |

* cited by examiner

BLOOD PURIFICATION DEVICE

Priority is claimed to Japanese Application No. 2002-330984 filed Nov. 14, 2002, and Japanese Application No. 2003-358200 filed Oct. 17, 2003.

BACKGROUND OF THE INVENTION

1. Field of the Invention

The present invention relates to a blood purification device which purifies blood from a patient in extracorporeal blood circulation.

2. Discussion of the Related Art

In dialysis treatment, a blood circuit consisting mainly of flexible tubing is used to place the blood of a patient in extracorporeal blood circulation. This blood circuit arrangement includes an arterial blood circuit having an arterial needle at one end to collect blood from the patient and a venous blood circuit having venous needle at one end to return the blood to the patient. A dialyzer can be incorporated between the arterial blood circuit and the venous blood circuit.

A roller blood pump is placed in the arterial blood circuit. By driving the pump, the blood of the patient is collected through the arterial needle and flows extracorporeally through the arterial blood circuit, the dialyzer, and the venous blood circuit. There are multiple hollow fibers inside the dialyzer. The blood flows through each hollow fiber.

Projections are formed on the dialyzer case, one being a dialysate inlet port and the other being a dialysate outlet port. Dialysate of predetermined concentration is supplied in through the dialysate inlet port, along the outside of the hollow fiber (i.e., between the outside surface of the hollow fibers and inside surface of the dialyzer case), and then out through the dialysate outlet port.

The walls of hollow fibers, which contain micropores, form blood purifying membranes. Waste products of the blood passing through the inside of the hollow fibers are dialyzed to the dialysate through the blood purifying membrane and the purified blood returns to the patient. To remove water from the blood of the patient during the dialysis treatment, the dialysis device includes a ultrafiltration pump.

Japanese laid open patent publication number H09-149935 disclosed a monitoring means for the amount of water to be removed which comprises a comparison between the real-time blood concentration measured and the blood concentration calculated from a blood flow rate of the blood pump and a water removal rate. The blood concentration (hematocrit value) measured from the passing blood through the dialyzer with one pair of a light emission means and a light reception means in the venous blood circuit.

As disclosed in the Japanese laid open patent publication number H0-149935, the blood purification device which measures the blood concentration from the passing blood through the dialyzer with the light sensor; monitors the amount of water to be removed by comparing between the real-time blood concentration measured while dialyzing and the theoretical value of the blood concentration calculated from the blood concentration measured prior to dialysis, a blood flow rate in the blood pump and a water removal rate. Accordingly, the errors regarding the amount of water removal are reduced, and consequently, the worsening of the patient's condition due to water removal error can be prevented.

OBJECT AND SUMMARY OF THE INVENTION

The object of the present invention is to eliminate pre-measurement of the blood concentration of a patient; reduce the burden on the patient by reducing time period for treatment; and to provide a blood purification device which monitors errors of various existing parameters.

Specifically, one prior art blood purification device employees a preset blood flow rate in the blood pump, a preset water removal rate, and a blood concentration measured prior to dialysis as parameters to obtain the theoretical value of the blood concentration; and accordingly the blood purification device needs to measure the blood concentration of a patient prior to dialysis, and accordingly the burden on the patient increases because of prolongation of a treatment period.

Further, the aforementioned prior art blood purification device monitors only an amount of removed water (deviation of water removal), but does not monitor various parameters existing in the device. Therefore, a device which can monitor the total device including blood circuit by measurement of the blood concentration is strongly desired.

The present invention provides a blood purification device including; a blood circuit having the arterial blood circuit and the venous blood circuit which circulate extracorporeally the blood collected from the patient; a blood pump disposed in the arterial blood circuit of the blood circuit; a blood purifier that is connected between the arterial blood circuit and the venous blood circuit, and purifies the blood flowing in the blood circuit; the first measuring means that is disposed in the arterial blood circuit of the blood circuit and measures the blood concentration of the arterial blood circuit; the second measuring means that is disposed in the venous blood circuit of the blood circuit and measures the blood concentration of the venous blood circuit; a calculating means that calculates the ratio of the blood concentrations measured by the first measuring means and the second measuring means, and the blood concentration ratio as a theoretical value obtained by designated formula using the preset blood flow rate of the blood pump and the blood purifying rate by the blood purifier as parameters; and a evaluation means whether the blood concentration ratio obtained from the calculating means as a measurement value and the blood concentration ratio as a theoretical value are roughly equal or not.

The present invention also provides the blood purification means as described above and includes a blood purifier that is connected between the arterial blood circuit and the venous blood circuit; the main blood purification device that includes a water removing means that is connected to the blood purifier and removes water from the blood flowing in the blood purifier; and the preset purifying rate which is the same as the water removal rate of the water removing means.

The present invention further provides the blood purification device including; a substitution fluid supplying means disposed to supply the substitution fluid into the blood circuit; and a calculating means that calculates the ratio of the blood concentrations calculated as a theoretical value by the designated formula using the preset substitution fluid supplying rate for the substitution fluid supplying means and a filtration rate for the blood purifying means in addition to the preset blood flow rate and the preset water removal rate as parameters.

The present invention also provides the blood purification device including; a reporting means that reports that the ratio difference between the blood concentration as the measurement value and the blood concentration as the theoretical value is bigger than the designated acceptable range by the evaluation means.

The blood purification device including; the steps of changing the blood flow rate, the purifying rate, the substitution fluid supplying rate and the filtration rate; and identifying a malfunction element if the ratio difference between the blood concentration as the measurement value by the evaluation means and the blood concentration as the theoretical value is bigger than the designated acceptable range by the evaluation means.

According to the invention both concentrations before the blood is introduced into the blood purifier and after the blood is removed from the blood purifier are measured respectively by the first measuring means in the arterial blood circuit and the second measuring means in the venous blood circuit, and accordingly not only the burden on the patient can be reduced with shorter treatment time because of no longer requirement for predetermination of the blood concentration of the patient, but also the malfunction of various parameters existing in the blood purification device can be monitored.

According to the invention, as the parameter is the water removal rate from the blood purifier and the main blood purification device for dialysis treatment, the invention can be appropriately applied to the dialysis treatment requiring water removal; and accordingly not only the burden on the patient can be reduced with shorter treatment time because of removing the longer requirement for predetermination of the blood concentration of the patient, but also the malfunction of various parameters existing in the blood purification device can be monitored.

Accordingly, the invention can be applied to the device such as HDF, HF and AFBF which supply the substitution fluid to the blood circuit; and accordingly not only the burden on the patient can be reduced with shorter treatment time because of no longer requirement for predetermination of the blood concentration of the patient, but also the malfunction of various parameters existing in the blood purification device can be monitored.

The invention can report, by the reporting means, that the ratio difference between the blood concentration as the measurement value and the blood concentration as the theoretical value is bigger than the designated acceptable number by the evaluation means; and accordingly the medical staff can recognize any malfunction on the blood purification device.

The invention can identify the malfunction element; and accordingly the medical staff can appropriately and smoothly response which means is needed to be fixed or repaired.

DETAIL DESCRIPTION OF THE PREFERRED EMBODIMENT

Figure 1:
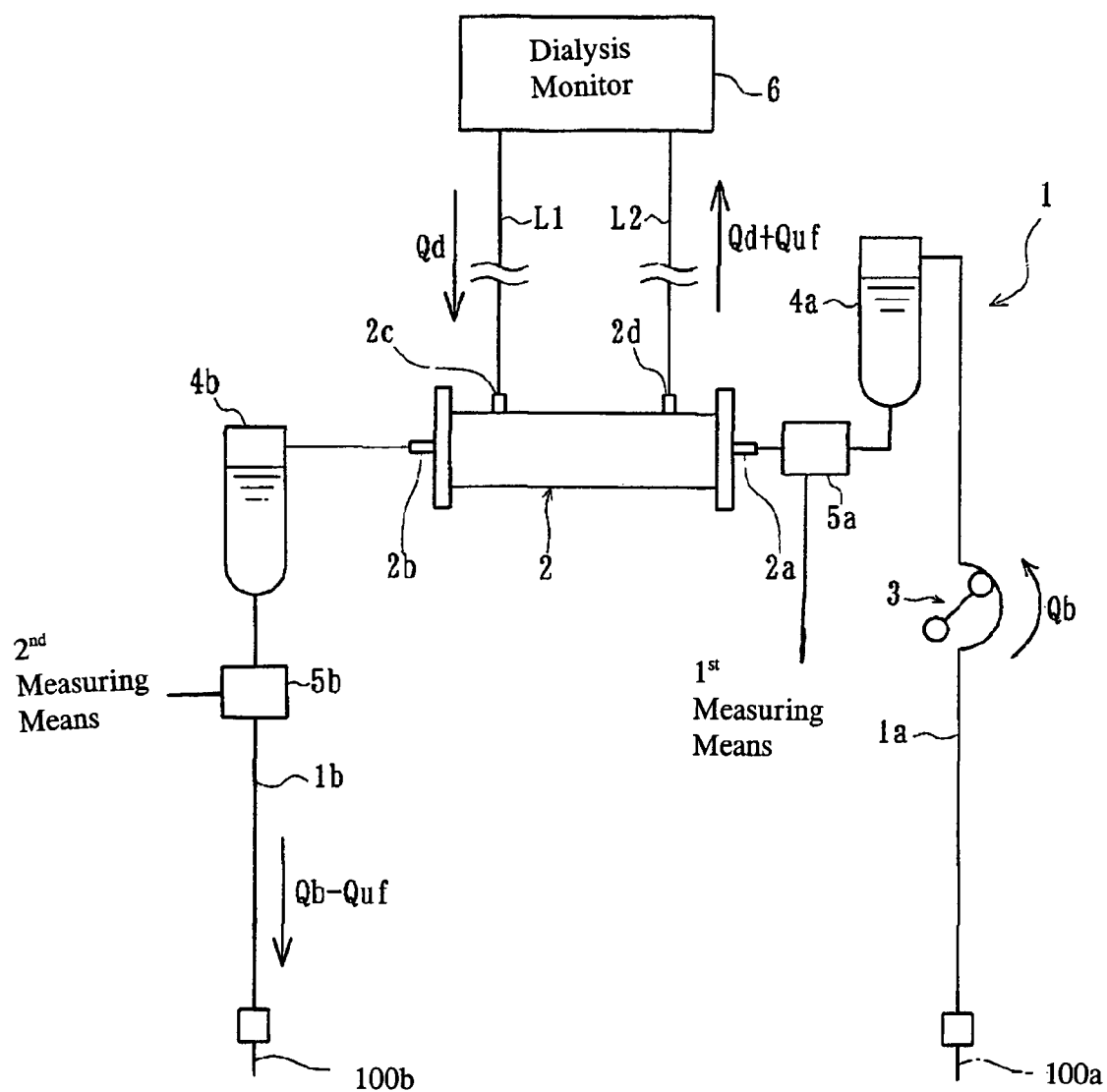
FIG. 1 is a schematic diagram of the blood purification device of the present invention.

The embodiments of the present invention are explained using the figures. The blood treatment device according to an embodiment includes a dialysis device that dialyzes the blood of a patient (HD) by extracorporeal circulation. The dialysis device includes, as shown in FIG. 1, a blood circuit attached a dialyzer 2 as a blood purifier; a dialysis monitor 6 that supplies the dialysate to the dialyzer 2 and remove water; a dialysate supplier 7 (see FIG. 2) that prepares the dialysate.

The blood purifier of the present invention includes the blood purification device of the present invention that includes the dialysis monitor 6 and the dialysate supplier 7; and the blood purifier (dialyzer 2). Specifically, the blood purifier is attached between an arterial blood circuit 1a and a venous blood circuit 1b; and purifies the blood running in the blood circuit 1.

The blood circuit 1 includes, as shown in FIG. 1, an arterial blood circuit 1a and a venous blood circuit 1b, which are made from flexible tubing. The dialyzer 2 acts as a blood purifier and is connected between the arterial blood circuit 1a and the venous blood circuit 1b.

An arterial needle 100a is attached to the end of the arterial blood circuit 1a, and a roller blood pump 3 and a drip chamber 4a are attached in the middle of the arterial blood circuit 1a. A venous needle 100b is attached to the end of the venous blood circuit 1b, and a drip chamber 4b is attached in the middle of the venous blood circuit 1b.

When the blood pump 3 is driven while the arterial needle 100a and the venous needle 100b are affixed to the patient, the blood of the patient flows through the arterial blood circuit 1a and into the dialyzer 2 after air bubbles are removed by the arterial drip chamber 4a. The dialyzer 2 purifies the blood. The blood flow out of the dialyzer 2 through the venous blood circuit 1b after air bubbles are removed by the venous drip chamber 4b and returns to the body of the patient. Thus, the blood of the patient is purified by the dialyzer 2 during extracorporeally circulating through the blood circuit 1.

Further, multiple rubber buttons (not shown in Fig.) can be attached in the middle of the venous blood circuit 1b or the arterial blood circuit 1a to introduce a drug fluid and collect a blood; and air bubble detector (not shown in Fig.) can be attached near the venous needle 100b in the venous blood circuit 1b to detect the presence of air in the venous blood circuit 1b.

Several ports are located on the case of the dialyzer 2; a blood inlet port 2a, a blood outlet port 2b, a dialysate inlet port 2c, and a dialysate outlet port 2d. The blood inlet port 2a and the blood outlet port 2b are connected to the arterial blood circuit 1a and the venous blood circuit 1b, respectively. The dialysate inlet port 2c and the dialysate outlet port 2d are connected to a dialysate inlet line L1 and a dialysate outlet line L2, respectively. Lines L1 and L2 extend from a dialysis monitor 6.

The dialyzer 2 includes multiple hollow fibers. The blood flows inside of the hollow fibers and the dialysate flows between the outside surface of the hollow fibers and the inside surface of the dialyzer case. The hollow fibers include many micropores that are located in the outside and the inside surfaces of the hollow fiber membrane, and through which waste products in the blood are dialyzed to the dialysate.

Figure 2:
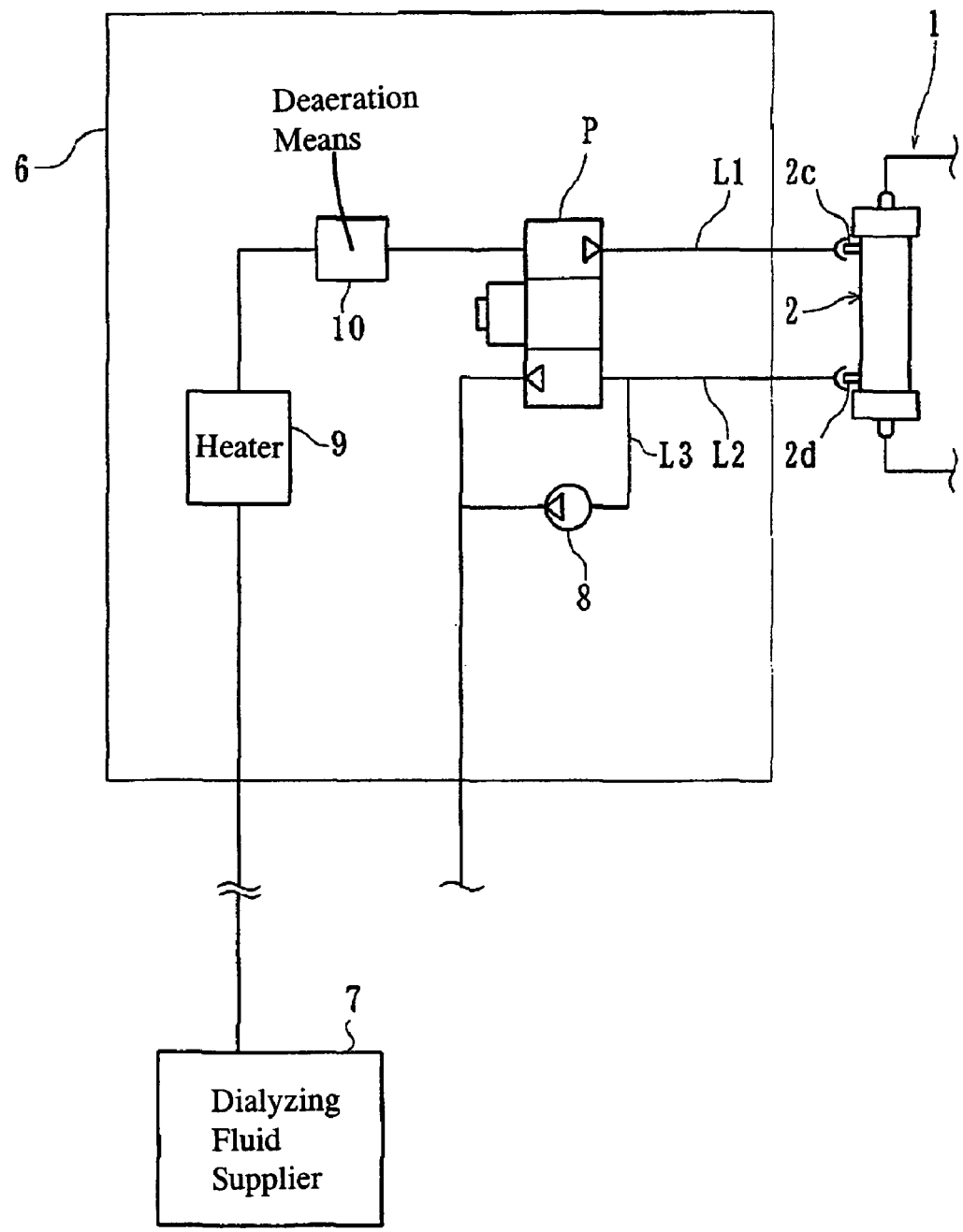
FIG. 2 is a schematic diagram of the dialysis monitor which is applied to the blood purification device of the present invention.

Further, as shown in FIG. 2, the dialysis monitor 6 includes a duplex pump P that is connected between the dialysate inlet line L1 and the dialysate outlet line L2. A bypass line L3 is connected to the dialysate outlet line L2, and bypasses the duplex pump P. An ultrafiltration pump 8 is connected to the bypass line L3. Additionally, one end of the dialysate inlet line L1 is connected to the dialysate inlet port 2c and the other end is connected to the dialysate supplier 7 which prepares the dialysate of the predetermined concentration.

One end of dialysate outlet line L2 is connected to the dialyzer 2 at the dialysate outlet port 2d. The other end of dialysate outlet line L2 is connected to a waste fluid disposal means (not shown in Fig.). The dialysate supplied from the dialysate supplier passes through the dialysate inlet line L1 to the dialyzer 2, the passed through the dialysate outlet line L2 and the bypass line L3, and is let out to the waste fluid disposal means. In FIG. 2, a heater 9 and a deaeration unit 10 are both connected to the dialysate inlet line L1.

The ultrafiltration pump 8 removes water from the blood of the patient flowing through the dialyzer 2. When the ultrafiltration pump is activated, the volume of dialysate let out of the dialysate outlet line L2 becomes greater than that of dialysate introduced from the dialysate inlet line L1 because the duplex pump P is quantitative; and water is removed from the blood by the difference of the inlet and outlet volumes. Instead of the ultrafiltration pump 8, other means (e.g. balancing chamber) can be used to remove water from the blood of the patient.

The first measuring means 5a is attached between the arterial drip chamber 4a in the arterial blood circuit 1a and the dialyzer 2 to measure the concentration (specifically, a hematocrit value) of the blood flowing in the arterial blood circuit 1a; and the second measuring means 5b is attached to the down stream side of the venous drip chamber 4b (the same side of the venous needle 100b) to measure the concentration (specifically, a hematocrit value) of the blood flowing in the venous blood circuit 1b.

The measuring means 5a and 5b include a hematocrit sensor. The hematocrit sensor, for example, contains a photo emitter, such as light emitting diode (LED), and a photo detector, such as a photo diode, and measures the hematocrit value that reflects the concentration of the patient's blood before the blood is introduced into the dialyzer 2 and after the blood is removed from the dialyzer 2, by emitting light (for example, near-infrared light of 805±15 nm wave length) toward the blood while at the same time detecting either pass-through or reflected light by the photo detector.

More specifically, the hematocrit value, which reflects the blood concentration, is obtained from the electronic signal output from the photo detector. The hematocrit value can be obtained by quantifying the red blood cells electronically optically based on the fact that blood components, such as red blood cells and plasma, have specific absorption spectra. The near-infrared emitted from the photo emitter, which is absorbed and scattered when being reflected by the blood, is received by the photo detector. The light absorption and scattering coefficient is analyzed based in the intensity of the light detected by the photo detector and thereby used to calculate the hematocrit value.

Figure 3:
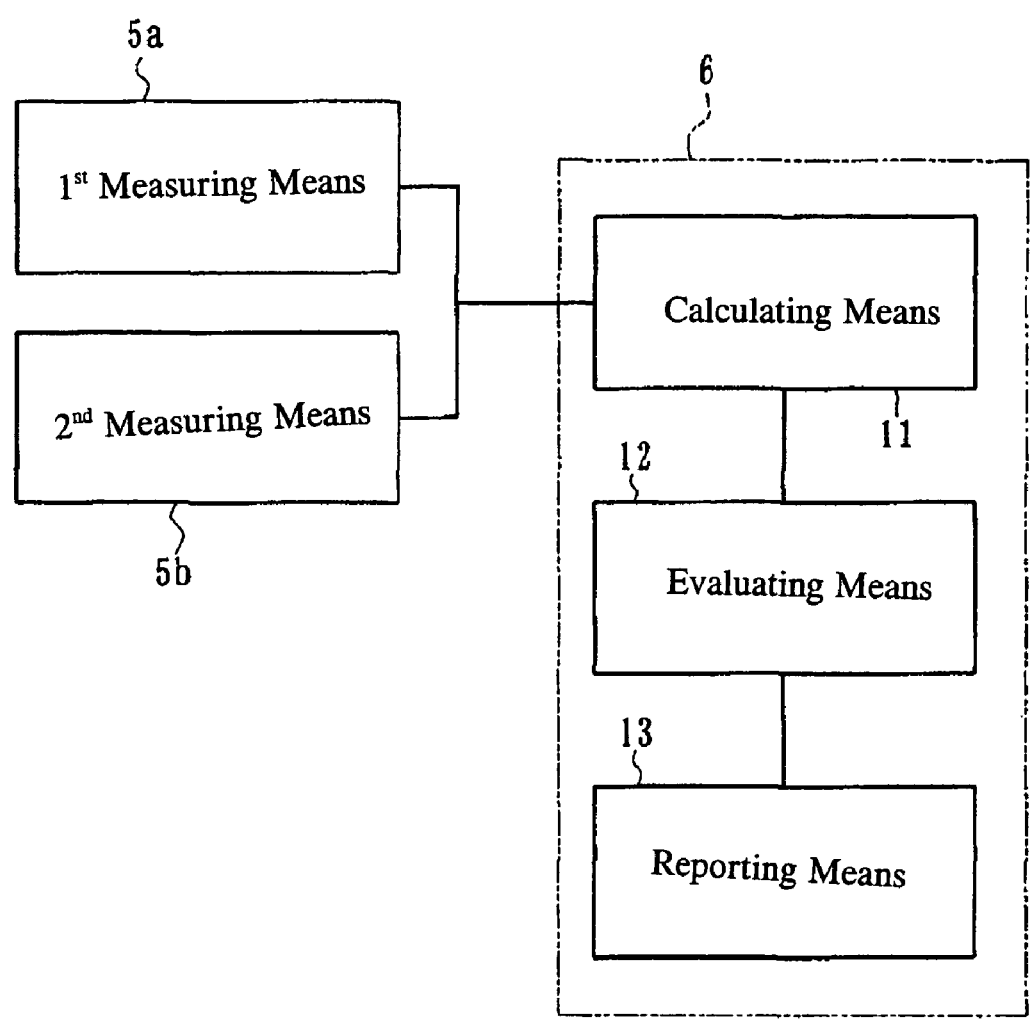
FIG. 3 is a block diagram of the blood purification device of the present invention.

The first measuring means 5a and the second measuring means 5b are electrically connected, as shown in FIG. 3, to the calculating means 11, the evaluating means 12 and the reporting means 13. The hematocrit value measured by the first measuring means 5a and the second measuring means 5b is sent as electronic signal to the calculating means 11. Either the microcomputer of the dialysis monitor 6 or another computer can be used as the calculating means 11 and/or the evaluating means. The reporting means can emit the photo emitting means with LED and display on the LCD screen, or output an alert from a speaker.

The calculating means 11 calculates the ratio of the hematocrit values measured by the first measuring means 5a and the second measuring means 5b, and the theoretical hematocrit value ratio obtained by designated formula using the preset blood flow rate of the blood pump 3 and the preset water removal rate of the ultrafiltration pump 8 (the preset blood purifying rate by the blood purifier) as parameters. If, for example, the hematocrit value measured by the first measuring means 5a is Hta, and the hematocrit value measured by the second measuring means 5b is Htv, the calculating means 11 calculate a measured ratio Hta/Htv; if the preset blood flow rate of the pump 3 is Qb and the water removal rate of the ultrafiltration pump 8 is Quf, the theoretical ratio Hta/Htv is calculated by the following formula.

There is the following relationship: Hta (theoretical value)×Qb(preset value)=Htv (theoretical value)×/Qb(preset value)−Quf(preset value)), Therefore, the theoretical value ratio is; Hta/Htv=1−(Quf (preset value)/Qb(preset value))

The calculating means calculates the theoretical value ratio calculated by the above formula and the above measured value ratio. The embodiment calculates the hematocrit value ratio (both measured and ideal) as Hta/Htv, but the inverse ratio Htv/Hta also can be used.

The evaluating means 12 evaluates whether the measured hematocrit value ratio and the theoretical hematocrit value ratio are roughly equal or not. The evaluation, for example, is carried out by determining whether a ratio of both ratios is approximately 1; or whether a difference between both ratios is close to 0. Preferably, the evaluation means 12 evaluates whether the ratio or the difference is out of a preset acceptable range estimated by possible measurement deviation.

If the blood pump 3 and the ultrafiltration pump 8 are correctly working; there is no trouble such as liquid leaking; and Qb and Quf are following the preset value, the theoretical hematocrit value ratio and the measured hematocrit value ratio must be the same and the relationship must be Hta/Htv (measured value)=1−Quf(preset value)/Qb(preset value). Thus, if the evaluating means determines that such relationship exists, it will be judged as there is no trouble in the dialysis device including the blood circuit 1. If the evaluating means determines that such relationship does not exist, it will be judged as a trouble condition in such as the blood pump 3 and/or the ultrafiltration pump 8 and accordingly the reporting means 13 reports the abnormality to, for example, medical staff.

When the reporting means 13 reports a trouble condition, both pumps are stopped and necessary repair and/or replacement should be carried out. Thus, as the reporting means 13 reports any trouble on such the blood pump 3 or the ultrafiltration pump 8, the medical staff can be notified of a trouble condition with the dialysis device.

If the relationship of Hta/Htv(measured value)=1−Quf (preset value)/Qb(preset value) does not exist and the right side value (i.e. theoretical value) is smaller than the left side value, it is considered either the driving rate of the ultrafiltration pump 8 is greater than the preset rate or the driving rate of the blood pump 3 is smaller than the preset rate. In both cases, it cannot be identified any pump which is in trouble. When the evaluating means 12 determines any trouble, the calculation means calculates in accordance with the following formula.

If the relationship, Hta/Htv(measured value)=1−Quf(preset value)/Qb(preset value) does not exist; then 1−Quf(preset value)/Qb(preset value)≠1−Quf (actual value)/Qb(actual value), and accordingly an equation; (Quf(preset value)/Q (preset value))/(Quf(actual value)/Qb(actual value)=p (p≠1) exists (hereinafter equation (1)).

Therefore, while the ultrafiltration pump 8 is kept at one preset flow rate, the flow rate of the pump 3 is altered by multiplying x times to Qb(preset value) (as Qb is known, xQb is also known); consequently, if Qb(actual value) is assumed multiplied y times, a relationship: Quf(preset value)/xQb (preset value))/(Quf(actual value)/yQb(actual value))=(y/x)p can exist (hereinafter equation (2)).

In this case, the blood pump 3 is functioning normally, the relationship x=y can exist, and accordingly the value from the equation (1) and the value from the equation (2) must be equal, but if both values are not equal, it can be determined that the blood pump 3 is abnormal.

On the other hand, while the blood pump 3 is kept at the preset flow rate, the flow rate of the ultrafiltration pump 8 is altered by multiplying a times to Quf(preset value); consequently, if Quf(actual value) is assumed multiplied b times, a relationship: (aQuf(preset value)/Qb(preset value))/(bQuf(actual value)/Qb(actual value))=(a/b) can exist (hereinafter equation (3)).

In this case, the blood pump 3 is functioning normally, the relationship a=b can exist, and accordingly the value from the equation (1) and the value from the equation (3) must be equal, but if both values are not equal, it can be determined that the ultrafiltration pump 8 is abnormal.

In other words, Hta(theoretical value)/Htv(theoretical value)=1−(Quf(preset value)/Qb (preset value)), and Hta (measured value)/Htv(measured value)=1−(Quf (actual value)/Qb(actual value)) exist, and accordingly if either the blood pump 3 or the ultrafiltration pump 8 is abnormal, [Quf(preset value)/Qb(preset value)]/[Quf (actual value)/Qb(actual value)]=p(p≠1) can exist. Thus, Quf(actual value)/Qb(actual value)=1−Hta(measured value)/Htv(measured value) can exist.

Accordingly, p=[Quf(preset value)/Qb(preset value)]/[1−Hta(measured value)/Htv(measured value)] can exist and the value of p can be obtained from the known preset value and the known measured value. In continuation, only the driving rate (preset value) of the blood pump 3 is altered to xQb (x is constant, and accordingly xQb is known value). Consequently, if Qb(actual value) is assumed to be y times, [Quf (preset value)/xQb(preset value)]/[Quf(actual value)/yQb (actual value)]=(y/x)p can exists. Then, if in comparison with the above p and (y/x) p, p=(y/x)p, specifically if y/x=1 exists, y=x exists, and accordingly it can be determined that the blood pump 3 is not abnormal and the ultrafiltration pump 8 is abnormal. In contrast, if y/x≠1, specifically, y≠x exists, it can be determined that the blood pump 3 is abnormal.

The aforementioned embodiment uses the ratio to evaluate by the evaluating means 12, but the difference can be also used to evaluate by the following the procedure.

Specifically, as well as the ratio comparison, a difference ΔL1 between theoretical value and measured value that can be obtained from both equations, Hta/Htv(theoretical value)=1−(Quf(preset value)/Qb(preset value)) and Hta/Htv(measured value)=1−(Quf(actual value)/Qb(actual value) is calculated by the following equation; ΔL1=[1−Quf(preset value)/Qb(preset value)]−[1−Quf(actual value)/Qb(actual value)]=Quf (actual value)/Qb(actual value)−Quf(preset value)/Qb (preset value).

If both the ultrafiltration pump 8 and the blood pump 3 are functioning normally, ΔL1=0 should exist. If ΔL1≠0 exist in the equation to give the difference, it is determined either the ultrafiltration pump 8 or the blood pump 3 is not functioning normally. Therefore, if ΔL1≠0 exist, the driving rate (preset value) of the blood pump 3 is altered to multiply Qb(preset value) by a times (as the preset value is known aQb is also known.) Consequently, if Qb(actual value) is assumed to be b times, the difference ΔL2 can be obtained from the following equation. ΔL2=Quf(actual value)/bQb(actual value)−Quf (preset value)/aQb(preset value) If the blood pump 3 is functioning normally, a=b can exist; and accordingly ΔL1=aΔL2 (also=bΔL2) should exist. If the relationship does not exist, it is determined that the ultrafiltration pump 8 is not functioning normally. When, also, the driving rate of the ultrafiltration pump 8 is multiplied by a times, the difference can be obtained from above equation.

In other words, ΔL1=1−[Quf(preset value)/Qb(preset value)]−[1−(Quf(actual value)/Qb(actual value))]=[Quf(actual value)/Qb(actual value)]−[Quf(preset value)/Qb(preset value)]=[1−Hta(measured value)/Htv(measured value)]−[Quf(preset value)/Qb(preset value)] exist, and accordingly ΔL1 can be obtained from known preset value and real value (measured value). If ΔL1=0 exists, it can be determined that both the blood pump 3 and the ultrafiltration pump 8 are functioning normally; but if ΔL1≠0 exists, it can be determined that either the blood pump 3 or the ultrafiltration pump 8 is not functioning normally.

If ΔL1≠0 exist, the driving rate (preset value) of the blood pump 3 is altered to aQb (as a is constant, aQb is also known value.) Consequently, if Qb(actual value) is assumed to be b times, the difference ΔL2 can be obtained from the following equation. ΔL2=1−[Quf(preset value)/aQb(preset value)]−[1−[Quf(actual value)/bQb(actual value)]]=[Quf (actual value)/bQb(actual value)]−[Quf(preset value)/aQb(preset value)] can exist.

If the blood pump 3 is functioning normally, a=b should exist; accordingly aΔL2 can be calculated as: aΔL2=(a/b)[Quf (actual value)/Qb(actual value)]−[Quf(preset value)/Qb (preset value)]=ΔL1; or bΔL2=[Quf (actual value)/Qb(actual value)]−(b/a)[Quf(preset value)/Qb(preset value)]=ΔL1 can exist.

If ΔLa≠0, and aΔL2=ΔL1 or bΔL2=ΔL1 exist, it is determined that the ultrafiltration pump 8 is not functioning normally; and if aΔL2≠ΔL1 or bΔL2≠ΔL1 exist, it is determined that the blood pump 3 is not functioning normally.

If the blood pump 3 is functioning normally, a=b can exist; and accordingly ΔL1=aΔL2 (also=bΔL2) should exist. If the relationship does not exist, it is determined that the ultrafiltration pump 8 is not functioning normally. When, also, the driving rate of the ultrafiltration pump 8 is multiplied a times, the difference can be obtained from above equation.

According to an embodiment, not only the burden on the patient can be reduced with shorter treatment time because of dispensing with the requirement for predetermination of the hematocrit value of the patient, but also the malfunction of various parameters existing in the blood purification device can be monitored. The invention can identify the malfunction element; and as the malfunction element can be identified, the medical staff can appropriately and smoothly response which means is needed to be fixed or repaired.

Figure 4:
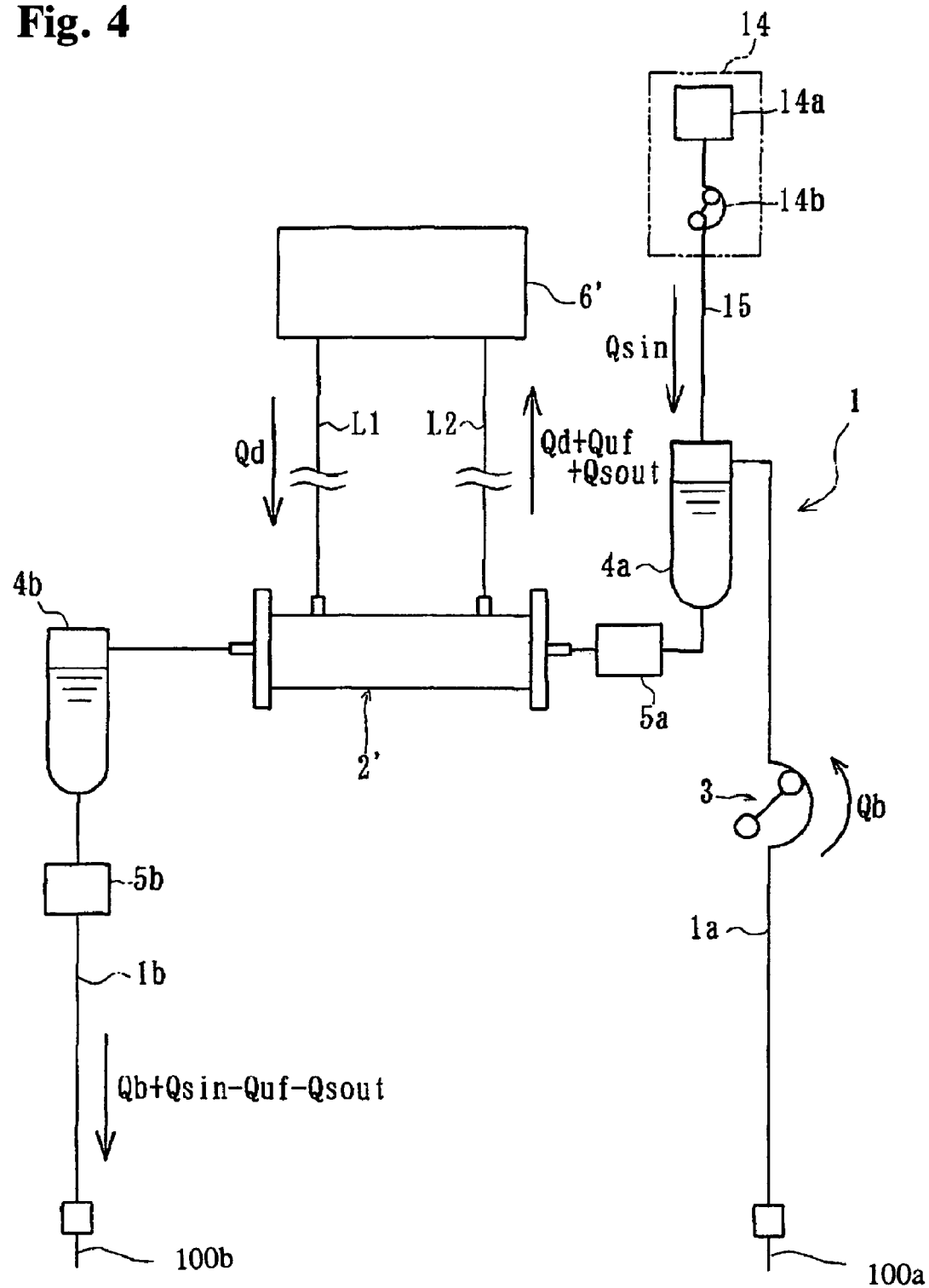
FIG. 4 is a schematic diagram of the blood purification device of another embodiment of the present invention.

According to another embodiment of the present invention, the blood purification device can be applied to the hemodiafiltration method (HDF) and the hemofiltration method (HF), wherein the substitution fluid is introduced from a arterial blood circuit; and as shown in FIG. 4, includes a blood circuit to which a blood purifier 2' including a filter is connected, and a main blood purification device 6' which is connected to the blood purifier 2' and can remove water. The same components in the above embodiment use the same numerals and the detail explanation for them is not described.

A substitution fluid introduction means 14, supplying the substitution fluid to the blood circuit 1, includes a substitution fluid bag 14a being able to store a designated amount of a substitution fluid is connected to the end of a substitution fluid introduction tube 15 made from a flexible tube which is extended from an arterial drip chamber 4a attached in the middle of the arterial blood circuit; and a roller substitution fluid pump 14b attached in the middle of the substitution fluid introduction tube 15.

As above, the first measuring means 5a and the second measuring means 5b, as shown in FIG. 3, are electrically connected to the calculating means 11, the evaluating means 12 and the reporting means 13. The calculating means 11 of the embodiment 2, calculates not only a hematocrit value ratio measured by the first measuring means 5a and the second measuring means 5b, but also a hematocrit value ratio as a theoretical value by using a designated equation with parameters including a preset blood flow rate of the blood pump 3, a preset water removal rate of the ultrafiltration pump 8, a substitution fluid rate of the substitution fluid means 14, and a filtration rate of the blood purifier 2'.

If, for example, Hta is a measured value by the first measuring means 5a, and Htv is a measured value by the second measuring means 5b, the calculating means 11 calculates the ratio, and if a preset blood flow rate of the blood pump 3 is Qb, a preset water removal rate of the ultrafiltration pump 8 is Quf, a substitution fluid rate of the substitution fluid means 14 is Qsin, and a filtration rate of the blood purifier 2' is Qsout, the calculating means 11 calculates the theoretical ratio of Hta/Htv by the following equation.

Hta(theoretical value)=Htp×[Qb/(Qb+Qsin)], and Htv (theoretical value)=Htp×[Qb/(Qb+Qsin−Quf−Qsout)]; wherein Htp is a hematocrit value of the eliminated blood, exist, and accordingly, the ratio of the above theoretical value can be obtained by the following equation: Hta/Htv(theoretical value)=1−[(Quf+Qsout)/(Qb+Qsin)]

In the case of HF, Qd=0 exists, and a general blood purification device can automatically control as Qsin=Qsout.

Accordingly, the calculating means 11 calculates the ratio of the theoretical value from the equation and the ratio of the measured value. As well as the previous embodiment, the evaluation means 12 determines whether both ratios are roughly equal or not. In the embodiment 2, the ratio of the hematocrit values (both measured value and ideal value) is Hta/Htv, but the inverse ratio Htv/Hta can also be applied.

If the blood pump 3 and the ultrafiltration pump 8 and the substitution fluid pump 14b are correctly working; there is no trouble such as liquid leaking; and Qb, Quf, Qsin and Qsout are following the preset value, the theoretical hematocrit value ratio and the measured hematocrit value ratio must be the same (Hta/Htv(measured value)=Hta/Htv (theoretical value), and the relationship must be Hta/Htv(measured value)= 1(Quf+Qsout)/(Qb+Qsin).

Thus, if the evaluating means 12 determines that such relationship exists, it will be judged as there is no trouble in the dialysis device including the blood circuit 1. If the evaluating means 12 determines that such relationship does not exist, it will be judged as there is some trouble in such as the blood pump 3, the ultrafiltration pump 8, and/or the substitution fluid introducing means 14, accordingly the reporting means 13 reports the abnormality to, for example, the medical staff.

If the relationship of Hta/Htv(measured value)=1−(Quf+Qsout)/(Qb+Qsin) does not exist and the right side value (theoretical value) is smaller than the left side value, it is considered either the flow rate of the ultrafiltration pump 8 is greater than the preset rate; the flow rate of the blood pump 3 is smaller than the preset rate; or the substitution fluid pump 14 is not functioning normally, or a liquid leaking to cause a shortage of the liquid replacement. In any case, it cannot be identified any pump which is in trouble. When the evaluating means 12 determines any trouble, the calculation means 11 calculates according to the following formula.

If the relationship, Hta/Htv(measured value)=1−(Quf+Qsout)/(Qb+Qsin) does not exist, 1−(Quf(preset value)+Qsout(preset value))/(Qb(preset value)+Qsin(preset value))≠ 1−(Quf(actual value)+Qsout(actual value))/(Qb(actual value)+Qsin(actual value));

and accordingly an equation, ((Quf(preset value)+Qsout(preset value))/(Qb(preset value)+Qsin((preset value))/((Quf(actual value)+Qsout(actual value))/(Qb(actual value)+Qsin(actual value))=q(q≠1) exists (hereinafter equation (4)).

Therefore, while the blood pump 3 and the substitution fluid pump 14 kept at the preset flow rate, the flow rate of the ultrafiltration pump 8 is altered by multiplying z times to Quf preset value)+Qsout(preset value); consequently, if Quf(actual value)+Qsout ((actual value) is assumed multiplied by s times (in the preset embodiment, the ultrafiltration pump 8 works on water removal and filtration), a relationship: [z(Quf (preset value)+Qsout(preset value))/(Qb(preset value)+Qsin (preset value))]/[s(Quf(actual value)+Qsout(actual value))/ (Qb(actual value)+Qsin(actual value))]=(z/s)q can exist (hereinafter equation (5)). In this case, the ultrafiltration pump 8 is functioning normally, the relationship z=s can exist, and accordingly the value from the equation (4) and the value from the equation (5) must be equal, but if both values are not equal, it can be determined that the ultrafiltration pump 8 is not functioning normally.

On the other hand, if the ultrafiltration pump 8 is functioning normally (in the case of that the ultrafiltration pump 8 is considered functioning normally), Quf(preset value)+Qsout (preset value)=Quf(actual value)+Qsout(actual value) can exist. Therefore, the equation (4) can be simplified as (Qb (actual value)+Qsin(actual value))/(Qb(preset value)+Qsin (preset value))=q(q≠1).

If only the substitution fluid and the filtration are stopped (as the same as HD in the previous embodiment; Quf(preset value) is as is; and Qsin and Qsout are zero, [Quf(preset value)/Qb(preset value)]/[Quf(actual value)/Qb(actual value)]=r(r≠1) can exist as the same as equation (1).

As HD described in the above embodiment, the preset value of the blood pump 3 is multiplied by x times, and then it is conformed by comparison that the blood pump 3 is not functioning normally. If the blood pump 3 is functioning normally, it is suspicious that the substitution fluid pump 14b is not functioning normally or a leak from the substitution fluid inlet tube 15 (substitution fluid circuit). An operator can visually recognize which the substitution fluid pump 14b is not functioning normally or another one is not functioning normally due to leaking from the substitution fluid circuit.

The aforementioned embodiment uses the ratio to evaluate by the evaluating means 12, but the difference can be also used to evaluate by the following procedure.

Specifically, as well as the ratio comparison, a difference ΔL3 between theoretical value and measured value that can be obtained from both equations: Hta/Htv(theoretical value)= 1−(Quf(preset value)+Qsout(preset value))/(Qb(preset value)+Qsin(preset value)) and Hta/Htv(measured value)=1− (Quf(actual value)+Qsout(actual value))/(Qb(actual value)+ Qsin(actual value)), is calculated by the following equation; ΔL3=(Quf(actual value)+Qsout(actual value))/(Qb(actual value)+Qsin(actual value))−(Quf(preset value)+Qsout(preset value)/(Qb(preset value)+Qsin(preset value)) (Hereinafter equation (A))

If the ultrafiltration pump 8 (or an independent filtration pump from a ultrafiltration pump), the blood pump 3 and the substitution fluid pump 14b are functioning normally, ΔL3=0 should exist. If ΔL3≠0 exist in the equation to give the difference, it is determined one of them is not functioning normally.

Therefore, if $\Delta L3 \neq 0$ exist, Quf(preset value)+Qsout(preset value) is multiplied by c times. Consequently, if Quf(actual value)+Qsout(actual value) is assumed to be d times, the difference $\Delta L4$ can be obtained from the following equation.

$\Delta L4$=d(Quf(actual value)+Qsout(actual value))/(Qb(actual value)+Qsin(actual value))−c(Quf(preset value)+Qsout(preset value))/(Qb(preset value)+Qsin(preset value))

If the ultrafiltration pump 8 and the independent filtration pump from a ultrafiltration pump are functioning normally, c=d can exist; and accordingly $\Delta L4$=c$\Delta L3$ (also=d$\Delta L3$) should exist. If the relationship does not exist, it is determined that the ultrafiltration pump 8 or the independent filtration pump from a ultrafiltration pump is not functioning normally.

If $\Delta L4$=c$\Delta L3$ (also=d$\Delta L3$) exists, the term of Quf+Qsout should not be involved because the preset value and the actual value are the same. Thus, $\Delta L3$ is simplified as $\Delta L3'$ which represents as $\Delta L3'$=1/(Qb(actual value)+Qsin(actual value))−1/(Qb(preset value)+Qsin(preset value))

When the substitution fluid pump 14b is stopped, the above simplified equation can be further simplified as $\Delta L3'$=1/Qb(actual value)−1/Qb(preset value). If $\Delta L3'$=0 exist in the equation, the blood pump 3 is functioning normally, but it is determined that the substitution fluid pump 14b is not functioning normally, or the substitution fluid introducing means 14 including the substitution fluid pump 14b has abnormality such as a liquid leaking. If $\Delta L3' \neq 0$ exist, it is determined that the blood pump 3 is not functioning normally.

Figure 5:
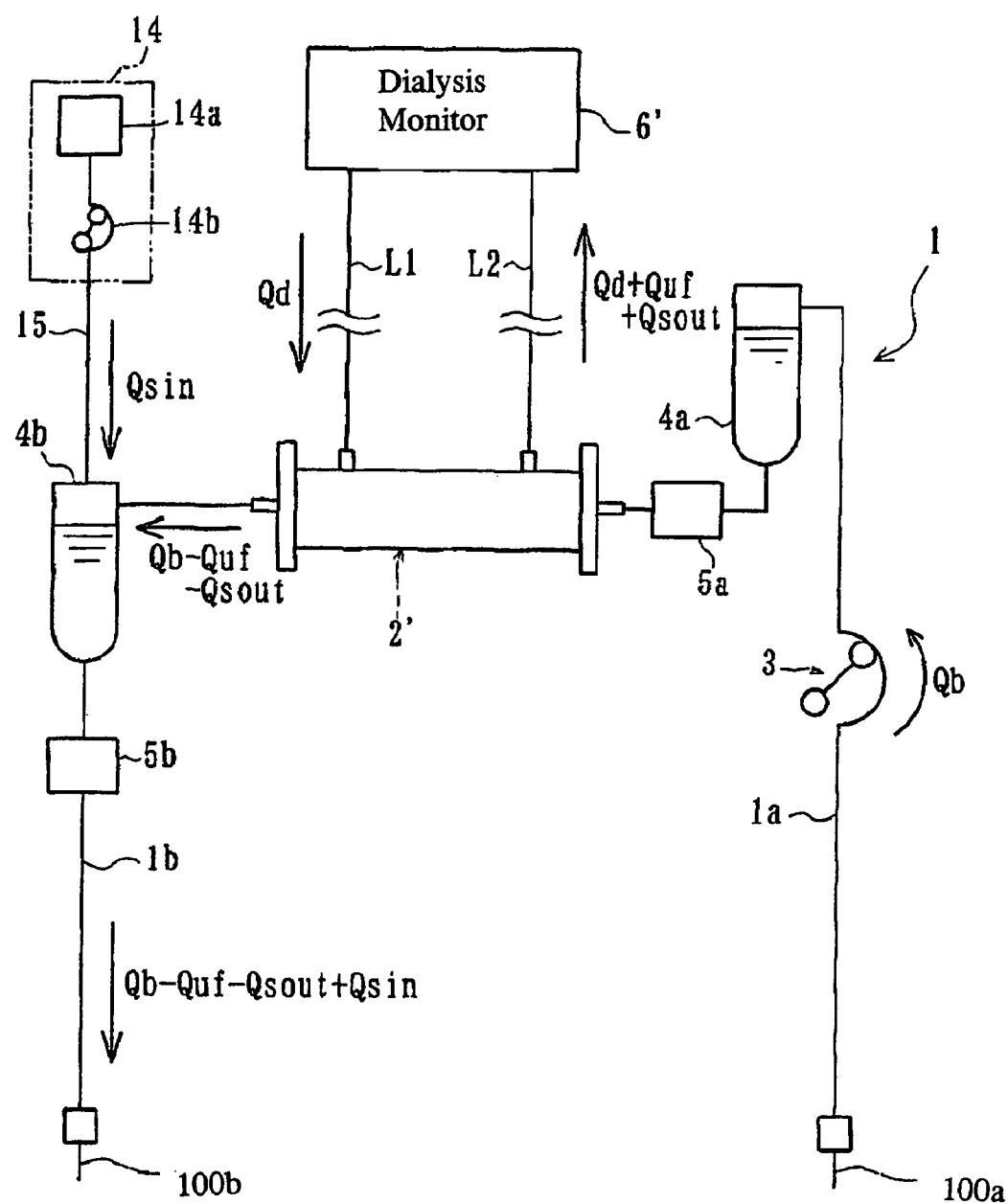
FIG. 5 is a schematic diagram of the blood purification device of another embodiment of the present invention.

According to another embodiment of the present invention, the blood purification device can be applied to the hemodiafiltration method (HDF), the hemofiltration method (HF), or an acetate-free biofiltration (AFBF), wherein the substitution fluid is introduced from a venous blood circuit; and as shown in FIG. 5, includes a blood circuit to which a blood purifier 2' including a filter is connected, and a main blood purification device 6' which is connected to the blood purifier 2' and can remove water. The same components as in the previous embodiments use the same numerals and the detail explanation for them is not described.

A substitution fluid introduction means 14 is connected to an venous drip chamber 4b attached in the middle of the venous blood circuit. The first measuring means 5a and the second measuring means 5b attached respectively in the arterial blood circuit 1a and the venous blood circuit 1b, as shown in FIG. 3, are electrically connected to the calculating means 11, the evaluating means 12 and the reporting means 13.

The calculating means 11, calculates not only a hematocrit value ratio measured by the first measuring means 5a and the second measuring means 5b, but also a hematocrit value ratio as a theoretical value by using a designated equation with parameters including a preset blood flow rate of the blood pump 3, a preset water removal rate of the ultrafiltration pump 8, a substitution fluid rate of the substitution fluid means 14, and a filtration rate of the blood purifier 2'.

Htp is a hematocrit value of the eliminated blood and the same as Hta meaning Htp=Hta. The calculating means 11 calculates as following; Htv(theoretical value)=Hta×Qb/(Qb+Qsin−Quf−Qsout); and accordingly, Hta/Htv(theoretical value)=1−(Quf+Qsout−Qsin)/Qb exist.

In the case of HF, Qd=0 exists, and a general blood purification device can automatically control as Qsin=Qsout.

The evaluation means 12 determines whether both ratios are roughly equal. If the blood pump 3, the ultrafiltration pump 8 and the substitution fluid pump 14b are correctly working; there is no trouble such as liquid leaking; the theoretical hematocrit value ratio and the measured hematocrit value ratio must be the same (Hta/Htv(measured value)=Hta/Htv(theoretical value), and the relationship must be Hta/Htv (measured value)=1−(Quf+Qsout−Qsin)/Qb.

Thus, if the evaluating means 12 determines that such relationship exists, it will be judged that the dialysis device including the blood circuit 1 is functioning properly. If the evaluating means 12 determines that such relationship does not exist, it will be judged as there is some trouble condition in such as the blood pump 3, the ultrafiltration pump 8, and/or the substitution fluid introducing means 14, accordingly the reporting means 13 reports the abnormality to such as medical staff.

If the relationship of Hta/Htv(measured value)=1−(Quf+Qsout−Qsin)/Qb does not exist and the right side value (theoretical value) is smaller than the left side value, it is considered either the flow rate of the ultrafiltration pump 8 is greater than the preset rate; the flow rate of the blood pump 3 is smaller than the preset rate; or the substitution fluid pump 14 is abnormal, or a liquid leaking to cause a shortage of the liquid replacement. In any case, it cannot be identified any pump which is not working properly. When the evaluating means 12 determines any trouble condition, the calculation means 11 calculates according to the following formula.

If the relationship, Hta/Htv(measured value)=1−(Quf(actual value)+Qsout(actual value)−Qsin(actual value))/Qb(actual value) does not exist, 1−(Quf(preset value)+Qsout(preset value)−Qsin(preset value))/Qb(preset value)$\neq$1−(Quf(actual value)+Qsout(actual value)−Qsin(actual value))/Qb(actual value), and accordingly an equation, [(Quf(preset value)+Qsout(preset value)−Qsin(preset value))/Qb(preset value)]/[(Quf(actual value)+Qsout(actual value)−Qsin(actual value))/(Qb(actual value)]=t(t$\neq$1) exists.

Therefore, while the ultrafiltration pump 8 and the substitution fluid pump 14 are kept at the preset flow rate, the flow rate of the blood pump 3 is altered by multiplying x times to Qb(preset value); consequently, if Qb(actual value) is assumed multiplied by y times, a relationship[(Quf(preset value)+Qsout(preset value)−Qsin(preset value))/xQb(preset value)]/[(Quf(actual value)+Qsout(actual value)−Qsin(actual value))/yQb(actual value)]=(y/x)t can exist (hereinafter equation (7)). In this case, the blood pump 3 is functioning normally, the relationship x=y can exist, and accordingly the value from the equation (6) and the value from the equation (7) must be equal, but if both values are not equal, it can be determined that the blood pump 3 is not functioning normally.

On the other hand, if the blood pump 3 is functioning normally (in the case of that the blood pump 3 is considered functioning normally), Qb(preset value)=Qb(actual value) can exist. Therefore, the equation (6) can be simplified as (Quf(preset value)+Qsout(preset value)−Qsin(preset value))/(Quf(actual value)+Qsout(actual value)−Qsin(actual value))= t(t$\neq$1) (hereinafter equation (8)).

Quf(preset value)+Qsout(preset value) are zero, and Qsin (preset value) is multiplied by c times. And consequently, if Qsin(actual value) is assumed to be d times, cQsin(preset value)/dQsin(actual value)=(c/d)t can exist (hereinafter equation (9)). If the substitution fluid pump 14b is functioning normally and there is no leaking from the substitution fluid introducing tube 15 (the substitution fluid circuit), the values of the equation (8) and (9) are equal and it is determined that the ultrafiltration pump 8 is not functioning normally.

If the values of the equation (8) and (9) are not equal, it may indicate problems with the substitution fluid pump 14b or leaking from the substitution fluid inlet tube 15 (substitution fluid circuit). An operator can visually recognize if the substitution fluid pump 14b is not functioning normally or another one is not functioning normally due to leaking from the substitution fluid circuit.

The aforementioned embodiment uses the ratio to evaluate by the evaluating means 12, but the difference can be also used to evaluate by the following procedure.

Specifically, as well as the ratio comparison, a difference $\Delta L5$ between theoretical value and measured value that can be obtained from both equations, Hta/Htv(theoretical value)= 1−(Quf(preset value)+Qsout(preset value)−Qsin(preset value))/Qb(preset value) and Hta/Htv(measured value)=1− (Quf(actual value)+Qsout(actual value)−Qsin(actual value))/ Qb(actual value), is calculated by the following equation; 66 L5=(Quf(actual value)+Qsout(actual value)−Qsin(actual value))/Qb(actual value)−(Quf(preset value)+Qsout(preset value)−Qsin(preset value))/Qb(preset value) (Hereinafter equation (B))

If the ultrafiltration pump 8 (or an independent filtration pump from a ultrafiltration pump), the blood pump 3 and the substitution fluid pump 14b are functioning normally, $\Delta L5=0$ should exist. If $\Delta L5 \neq 0$ exist in the equation to give the difference, it is determined that one of the pumps is not functioning normally. Therefore, if $\Delta L5 \neq 0$ exist, Qb(preset value) is multiplied by e times. Consequently, if Qb(actual value) is assumed to be f times, the difference $\Delta L6$ can be obtained from the following equation. $\Delta L6$=(Quf(actual value)+Qsout (actual value)−Qsin(actual value))/fQb(actual value)−(Quf (preset value)+Qsout(preset value)−Qsin(preset value))/eQb (preset value). If the blood pump 3 is functioning normally, e=f can exist; and accordingly $\Delta L5 = e\Delta L6$ (also=$f\Delta L6$) should exist. If the relationship does not exist, it is determined that the blood pump 3 is not functioning normally.

If $\Delta L5 = e\Delta L6$ (also $f\Delta L6$) exists, Qb(preset value) and Qb(actual value) are equal and should not be involved Thus, $\Delta L5$ is simplified as $\Delta L5'$ which represents as $\Delta L5'$=(Quf (actual value)+Qsout(actual value)−Qsin(actual value))− (Quf(preset value)+Qsout(preset value)−Qsin(preset value)).

When the substitution fluid pump 14b is stopped, the above simplified equation can be further simplified as $\Delta L5'$=(Quf (actual value)+Qsout(actual value))−(Quf(preset value)+ Qsout(preset value)). If $\Delta L5'=0$ exist in the equation, the ultrafiltration pump 8 and the independent filtration pump from a ultrafiltration pump, but it is determined that the substitution fluid pump 14b is not functioning normally, or the substitution fluid introducing means 14 including the substitution fluid pump 14b has abnormality such as a liquid leaking. If $\Delta L5' \neq 0$ exist, it is determined that the ultrafiltration pump 8 and the independent filtration pump from an ultrafiltration pump are not functioning normally.

According to the embodiment includes the substitution fluid to the arterial blood circuit la and the embodiment includes the substitution fluid to the venous blood circuit 1b, HDF or HF and one embodiment includes AFBF, in the case of introduction of the substitution fluid, not only the burden on the patient can be reduced with shorter treatment time because of no longer requirement for predetermination of the blood concentration of the patient, but also the malfunction of various parameters existing in the blood purification device (specifically troubles on the blood pump, the ultrafiltration pump, the substitution fluid pump and leaking from the substitution fluid introducing means) can be monitored.

Figure 6:
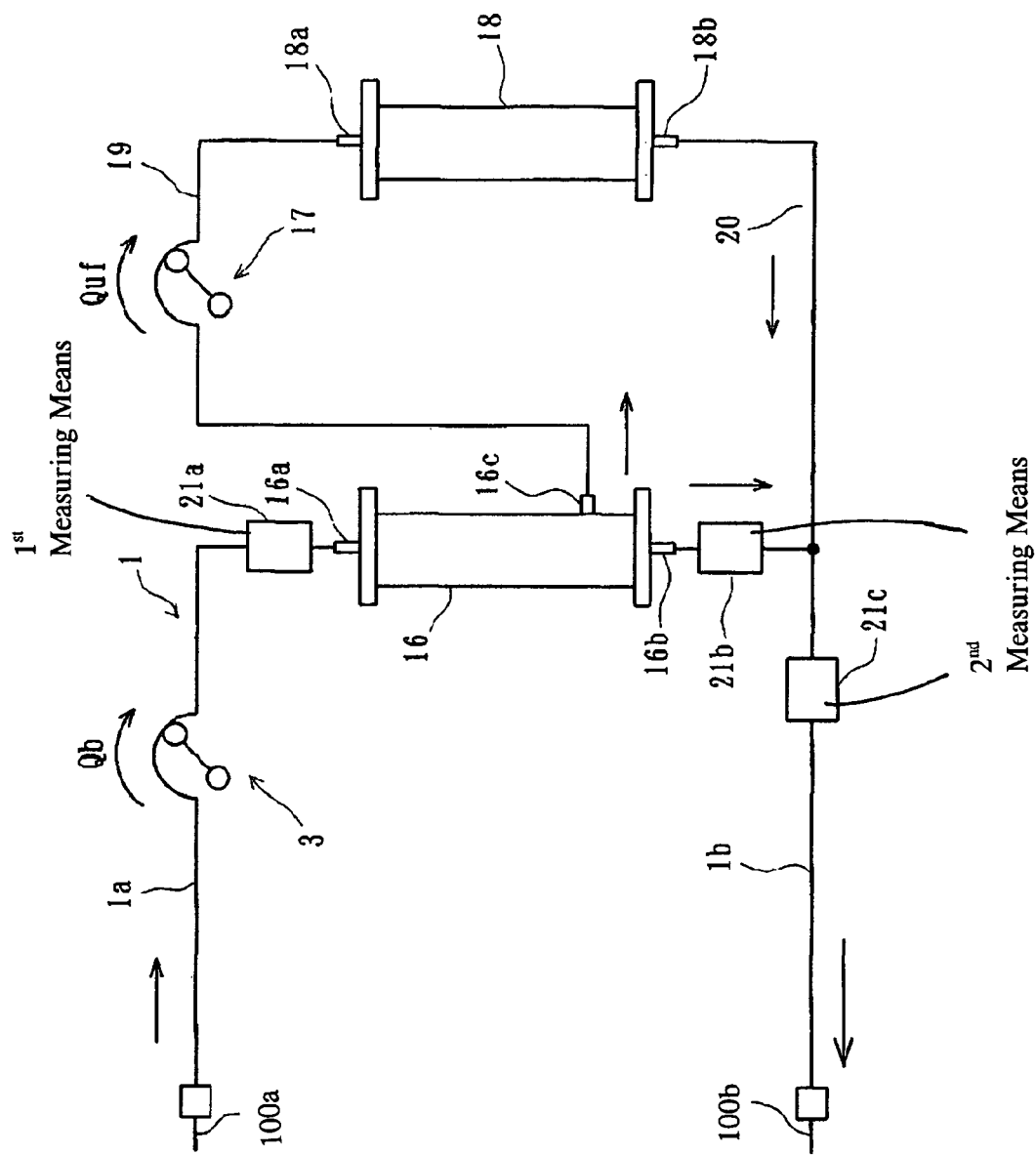
FIG. 6 is a schematic diagram of the blood purification device of another embodiment of the present invention.

According to a further embodiment, the blood purification device includes a plasma adsorption device which carries out a plasma separation process to separate plasma from the patient's blood circulating extracorporeally; and an adsorption process to selectively adsorb and eliminates substances related to illness from the separated plasma; as shown in FIG. 6, also includes the blood circuit 1 comprising the arterial blood circuit 1a and the venous blood circuit 1b; a plasma separator 16, a plasma pump 17, a adsorption column 18, the first measuring means 21a and the second measuring means 21b and 21c. The same components in the previous embodiment use the same numerals and the detail explanation for them is not described.

The plasma separator 16 having inside multiple hollow fibers which is the same as one used in a dialyzer (in general, the membrane pore size for the separator is bigger than one for a dialyzer) is connected between the arterial blood circuit 1a and the venous blood circuit 1b. Specifically, the separator 16 includes a blood inlet port 16a attached to the arterial blood circuit 1a; a plasma outlet port 16c to drain the plasma (liquid components) passed through the pores of hollow fiber; a blood cells outlet port 16b attached to the venous blood circuit to drain the blood cells components such as red blood cells passed through the inside hollow fibers, and the plasma which was not drained from the plasma outlet port 16c.

One end of the plasma inlet line 19 is connected to the plasma outlet port 16c, and the other end of the plasma inlet line 19 is connected to the plasma inlet port 18a on the adsorption column 18. The roller type plasma pump 17 as the same as the blood pump 3 is attached in the middle of the plasma inlet line 19 to suck the plasma from the plasma separator 16 to the adsorption column 18.

An adsorbent to selectively adsorb plasma substances related to illness is packed in inside of the adsorption column which has a plasma inlet port 18a at upper part and a plasma outlet port 18b at lower part. The plasma outlet port 18b is connected to one end of the plasma outlet line 20; wherein the other end of the plasma outlet line 20 is connected to the designated part of the venous blood circuit. The blood purifier comprised the plasma separator 16 and the adsorption column 18.

The first measuring means 21a and the second measuring means 21b and 21c include a hematocrit sensor to measure the blood concentration (i.e. hematocrit value). The first measuring means 21a is attached to the arterial blood circuit 1a (i.e. the upper stream of the plasma separator 16) and the second measuring, means 21b and 21c are attached to the venous blood circuit (i.e. the lower stream of the plasma separator 16). Further, the second measuring means 21b is attached in the upper stream of the connection point of the venous blood circuit 1b and the plasma outlet line 20, and the second measuring means 21c is attached in the lower stream of the above connection point.

The aforementioned the first measuring means 21a, the second measuring means 21b and 21c are electrically connected to the calculating means, the evaluating means and the reporting means (as shown in FIG. 3). The calculating means calculates the ratio of the blood concentration measured by the first measuring means 21a and the second measuring means 21b, or by the first measuring means 21a and the second measuring means 21c; and the ratio of the theoretical values of the blood concentration obtained from a designated formula using the preset blood flow rate and the filtration rate by the plasma separator (the blood purifying rate) as parameters.

As well as the above embodiment, the evaluating means determines whether the ratio of the measured blood concentration and the ratio of the theoretical blood concentration calculated by the calculation means are equal or not. The reporting means reports that the difference between the ratio of the measured blood concentration and the ratio of the theoretical blood concentration calculated is in or out of the designated acceptable range by the evaluation means.

The following is an explanation of the action of the plasma adsorption apparatus.

The arterial needle 100a and the venous needle 100b formed at both ends of the blood circuit 1 are injected to the patient, the blood pump 3 is set to the preset flow rate Qb and also the plasma pump 17 is set to the preset flow rate Quf. Accordingly, the patient's blood flows through the arterial blood circuit 1a from the arterial needle 100a to the first measuring means 21a; wherein the blood concentration (the hematocrit value) of the patient's blood is measured by the first measuring means 21a, and then the blood is introduced into the plasma separator 16.

In the process of passing the plasma separator 16, the blood cell components such as red blood cells in the blood (including, as aforementioned, some plasma which are not drained from the plasma outlet port 16c. Hereinafter it is the same) are drained from the blood component outlet port 16b; the plasma in the blood is drained from the outlet port 16c by suction of the plasma pump 17, and is sent to the inside of the adsorption column 18 through the plasma inlet line 19. Quf is the filtration rate of the plasma (preset purifying rate) drained from the plasma outlet port 16c.

After the plasma sent into the adsorption column is purified by the adsorbent to selectively adsorb and eliminate the substances related to illness, the plasma is drained from the plasma outlet port 18b and then sent to the venous blood circuit 1b through the plasma outlet line 20. The blood cell components drained from the plasma separator and the purified plasma drained from the adsorption column 18 are returned to the patient's body through the venous needle 100b.

The blood concentration (hematocrit value) of the blood drained from the plasma separator 16 is immediately measured by the second measuring means 21b (i.e. before combined with the plasma drained from the adsorption column 18), the blood concentration of the combined blood with the plasma is measured by the second measuring means 21c. The calculating means calculates the ratio of the first measuring means 21a and the second measuring means 21b (theoretical value ratio and measured value ratio), and the ratio of the first measuring means 21a and the second measuring means 21c (theoretical value ratio and measured value ratio) and the evaluating means determines whether these ratio are equal or not. The methods to calculate and evaluate each ratio are the same as in the initial embodiment.

If the blood pump 3 and the plasma pump 17 are functioning normally; there is no leaking; and Qb and Quf are correctly set, the evaluating means determines that each ratio is roughly equal. If there is a trouble condition with the pumps or any leaking, the evaluating means determines that at least one of the ratios is not roughly equal, and the reporting means reports an abnormality to the medical staff.

When the abnormality is evaluated, it is preferred to identify the malfunction part by alternating the blood flow rate Qb of the blood pump 3 and/or the filtration rate Quf of the plasma pump 17. According to the embodiment, two second measuring means 21b and 21c are connected, but also it is acceptable that only one of them is connected. Thus, the second measuring means 21c is connected at the lower stream than the connecting point of the venous blood circuit 1b and the plasma outlet line 20, and accordingly when the blood concentration measured by the measuring means 21a attached at the upper stream of the plasma separator is compared, any leaking from the blood circuit 1 can be detected.

The present invention is not limited to the blood purification devices in accordance with these embodiments. The dialysis device, for example, applied in the embodiments is a kind of the central systems comprising separately a dialysate supplier and a dialysis monitor, but also the present invention can be applied to the unified system (i.e. a personal dialysis unit).

The duplex pump in the dialysis monitor supplies the dialysate to the dialyzer 2, but a balancing chamber without a duplex pump can also be used. Further, a double needle having an arterial needle 100a and a venous needle 100b in the blood circuit is used, but a single needle having one needle can also be used.

The present invention can be applied to the plasma adsorption method, but also can be applied to other method different from the plasma adsorption method (i.e. the plasmapheresis method that is a double filtration plasmapheresis which separates passable substances and impassable substances through the membrane pores.) In addition, the present invention can be applied to a plasmapheresis method, which returns the replaced liquid replacement while the plasma separated is being removed.

According to the present invention, the first measuring means and the second measuring means measure a hematocrit value as the blood concentration, but also other parameter representing the blood concentration can be measured. Instead of the blood concentration, for example, a hemoglobin concentration (g/dL) considering the hemoglobin in the red blood cells can be used. It can be considered that the hemoglobin mass does not change during water removal and filtration by a dialysis device or the plasma separator. (i.e. all red blood cells can be passed through the plasma separator.) If after or before water removal and filtration, each hemoglobin concentrations are Hba and Hbv(g/dL); the blood flow rate passing into the blood purifier or the plasma separator is Qb(dL/min); and the water removal rate or the filtration rate is Quf(dL/min), a ratio, Hba/Hbv=1−Qb/Quf, of the theoretical value can be obtained by using the relationship formula, Hba(g/dL)×Qb(dL/min)×t(min)=Hbv(g/dL)×(Qba−Quf)(dL/min)−t(min). The evaluation means determines based on such theoretical ratio and measured ratio, and the blood purification device (including the dialyzer and the plasma separation device) monitors the malfunction of the existing various parameters.

Further, a hemoglobin mass per unit of blood mass is used as a benchmark of the concentration (g/kg). If the blood concentrations before and after water removal and filtration are Xa and Xv (g/kg), the blood flow rate (mass flow rate) into the blood purifier or the plasma separator is Qbm(kg/min), the water removal rate or the filtration rate is Qufm, the theoretical ratio, Xa/Xv=1−Qbm/Qufm, can be obtained by using the relationship formula, Xa(g/kg)×Qbm(kg/min)×t(min)=Xv(g/kg)×(Qbm−Qufm)(kg/min)×t(min). The evaluation means determines based on such theoretical ratio and measured ratio, and the blood purification device (including the dialyzer and the plasma separation device) monitors the malfunctions of the existing various parameters.

The ratio of the blood concentration can be represented by mass/volume concentration ratio and mass/mass concentration ratio. Nevertheless hematocrit and hemoglobin concentration, the representation can be applied to the concentration based on other benchmarks. Further, in the other embodiments, the representation can be applied to an online HDF and an online HF.

Further, the operation to compare the ratio of measured blood concentration and theoretical blood concentration can be automatically carried out, or continuously carried out (periodically repeated). If the size of the blood cells is affected by an osmotic pressure depending on the plasma and dialysate concentration, the comparison can be carried out after some compensation. (e.g. the method using the dialysate concentration value measured by the dialysis device.)

The present invention can be applied to the various blood purification devices to extracorporeally purify the patient's blood.

We claim:

1. A blood purification device comprising:
   a blood circuit having an arterial blood circuit and a venous blood circuit;
   a blood pump disposed in said arterial blood circuit, the blood pump being operable to provide a preset blood flow rate Qb;
   a blood purifier connected to the blood circuit between said arterial blood circuit and said venous blood circuit, and configured to purify blood flowing in said blood circuit, the blood purifier being operable to provide a preset water removal rate Quf;
   a first measuring unit disposed in said arterial blood circuit wherein said first measuring unit measures a first hematocrit value Hta of said arterial blood circuit;
   a second measuring unit disposed in said venous blood circuit wherein said second measuring unit measures a second hematocrit value Htv of said venous blood circuit;
   a calculating unit configured to calculate a measured ratio value and a theoretical ratio value, and then to calculate an evaluation value comparing a closeness of the measured ratio value to the theoretical ratio value, wherein:
   the first measured hematocrit value Hta is divided by the second measured hematocrit value Htv to obtain the measured ratio value Hta/Htv, and
      the preset water removal rate Quf is divided by the preset blood flow rate Qb to obtain the theoretical ratio value 1−Quf/Qb;
   an evaluation unit coupled to the calculating unit and configured to evaluate whether the evaluation value is larger than a predetermined value; and
      a reporting unit configured to report a trouble condition indicating a malfunction for at least one of said blood pump and said blood purifier when the evaluation value, based on the first measured hematocrit value Hta and the second measured hematocrit value Htv, is larger than the predetermined value; wherein
   said blood pump is further configured to adjust the preset blood flow rate to an adjusted blood flow rate when the trouble condition exists;
   said calculating unit is further configured to calculate a second measured ratio value and a second theoretical ratio value, said second measured ratio value referring to a ratio of said blood concentrations measured by said first measuring unit and said second measuring unit while said blood pump is operated at said adjusted blood flow rate and said blood purifier is operated at said preset water removal rate, and said second theoretical ratio value referring to a blood concentration ratio obtained by at least one formula based on parameters including said adjusted blood flow rate of said blood pump and said preset water removal rate of said blood purifier;
   said evaluation unit is further configured to evaluate whether a difference between said second measured ratio value and said second theoretical ratio value indicates the trouble condition; and
   said reporting unit is further configured to report the trouble condition for said blood purifier when said difference between said second measured ratio value and said second theoretical ratio value is at a first value which differs from a second predetermined acceptable ratio difference, and to report the trouble condition for said blood pump when said difference between said second measured ratio value and second theoretical ratio value is at a second value which differs from the second predetermined acceptable ratio difference.

2. The blood purification device of claim 1, wherein:
   said blood purifier includes a water removing unit connected to said blood purifier; configured to remove water from blood flowing in said blood purifier.

3. The blood purification device of claim 2, further comprising:
   a substitution fluid supplying unit configured to supply a substitution fluid into said blood circuit, wherein
   said calculating unit configured to calculate a theoretical ratio value is based on parameters including a preset substitution fluid supplying rate of said substitution fluid supplying unit and a filtration rate of said blood purifier in addition to said preset blood flow rate and said preset water removal rate, and
   said reporting unit is configured to report a trouble condition for at least one of said blood pump, said blood purifier and said substitution fluid supplying unit.

* * * * *